(12) United States Patent
Patel

(10) Patent No.: US 9,327,094 B2
(45) Date of Patent: May 3, 2016

(54) APPARATUS FOR ASSISTING A CHILD TO FALL ASLEEP

(71) Applicant: Ashtel Studios, Inc., Fontana, CA (US)

(72) Inventor: Anish Patel, Fontana, CA (US)

(*) Notice: Subject to any disclaimer, the term of this patent is extended or adjusted under 35 U.S.C. 154(b) by 471 days.

(21) Appl. No.: 13/777,323

(22) Filed: Feb. 26, 2013

(65) Prior Publication Data
US 2014/0228622 A1   Aug. 14, 2014

Related U.S. Application Data

(60) Provisional application No. 61/762,850, filed on Feb. 9, 2013.

(51) Int. Cl.
*A61M 21/02* (2006.01)
*A63H 3/28* (2006.01)
*A61M 21/00* (2006.01)

(52) U.S. Cl.
CPC .............. *A61M 21/02* (2013.01); *A63H 3/28* (2013.01); *A61M 2021/005* (2013.01); *A61M 2021/0027* (2013.01); *A61M 2205/3592* (2013.01); *A61M 2205/59* (2013.01); *A63H 2200/00* (2013.01)

(58) Field of Classification Search
CPC ............... A61M 2021/0027; A61M 21/00; A61M 21/02; A61M 2205/3592; A61M 2205/59; A63H 2200/00; A63H 3/28
USPC ........................................ 600/27, 28
See application file for complete search history.

(56) References Cited

U.S. PATENT DOCUMENTS

| 4,846,693 | A | * | 7/1989 | Baer | 434/308 |
| 6,012,961 | A | * | 1/2000 | Sharpe et al. | 446/298 |
| 2008/0153384 | A1 | * | 6/2008 | Friedland et al. | 446/297 |
| 2011/0139945 | A1 | * | 6/2011 | Fahrberger | H04M 1/04 248/121 |

FOREIGN PATENT DOCUMENTS

JP   2011-056647   10/2012

* cited by examiner

*Primary Examiner* — Charles A Marmor, II
*Assistant Examiner* — Joshua D Lannu
(74) *Attorney, Agent, or Firm* — LeonardPatel PC

(57) ABSTRACT

One or more embodiments of the present invention pertain to an apparatus that helps a child to fall asleep. The apparatus includes a set of eyes and eye lids. The apparatus also includes a media input/output unit configured to output audio from the apparatus or a portable device. The eyelids are may be configured to close while the audio is outputted from the media input/output unit.

16 Claims, 9 Drawing Sheets

APPARATUS FOR ASSISTING A CHILD TO FALL ASLEEP

CROSS REFERENCE TO RELATED APPLICATIONS

This application claims the benefit of U.S. Provisional Application Ser. No. 61/762,850, filed on Feb. 9, 2013. The subject matter of this earlier filed provisional patent application is hereby incorporated by reference in its entirety.

FIELD

The present invention relates to an apparatus that assists a child to fall asleep using audio and visual effects.

BACKGROUND

It is often a difficult task for a parent to make his or her child fall asleep. To this end, the parent may use different tactics to get his or her child to sleep. Some of these tactics may include lying down with the child, reading a bedtime story, reading a story book, singing a song, watching videos with the child, or watching television. However, such tactics may be cumbersome and time consuming for the parent. Also, the parent may not have the time to perform such tasks due to his or her busy schedule. Thus, a sleep aid that assists a child in falling asleep and does not necessarily require parental action may be beneficial.

SUMMARY

Certain embodiments of the present invention may provide solutions to the problems and needs in the art that have not yet been fully identified, appreciated, or solved by current toys. For example, certain embodiments of the present invention may be directed to a character (hereinafter apparatus) configured to use audio and visual effects to help a child to fall asleep.

In one embodiment, an apparatus may include a set of eyes and eyelids. The apparatus may also include a timer configure to operate the apparatus for a predefined period of time. During operation of the apparatus, the apparatus is configured to cause the set of eyelids to close over the course of the predefined period of time.

In another embodiment, an apparatus may include a set of eyes and a set of eyelids, a media player/recorder, and a timer. The media player/recorder is configured to output audio via a speaker for a predefined period of time. The timer is configured to provide timing information to the media player/recorder and control a motor to move the set of eyelids for the predefined period of time. The timer is further configured to cause the media player/recorder to decrease a volume of the audio, and simultaneously cause the set of eyelids to close, over the course of the predefined period of time.

BRIEF DESCRIPTION OF THE DRAWINGS

In order that the advantages of certain embodiments of the invention will be readily understood, a more particular description of the invention briefly described above will be rendered by reference to specific embodiments that are illustrated in the appended drawings. While it should be understood that these drawings depict only typical embodiments of the invention and are not therefore to be considered to be limiting of its scope, the invention will be described and explained with additional specificity and detail through the use of the accompanying drawings, in which.

DETAILED DESCRIPTION OF THE EMBODIMENTS

Figure 1A:
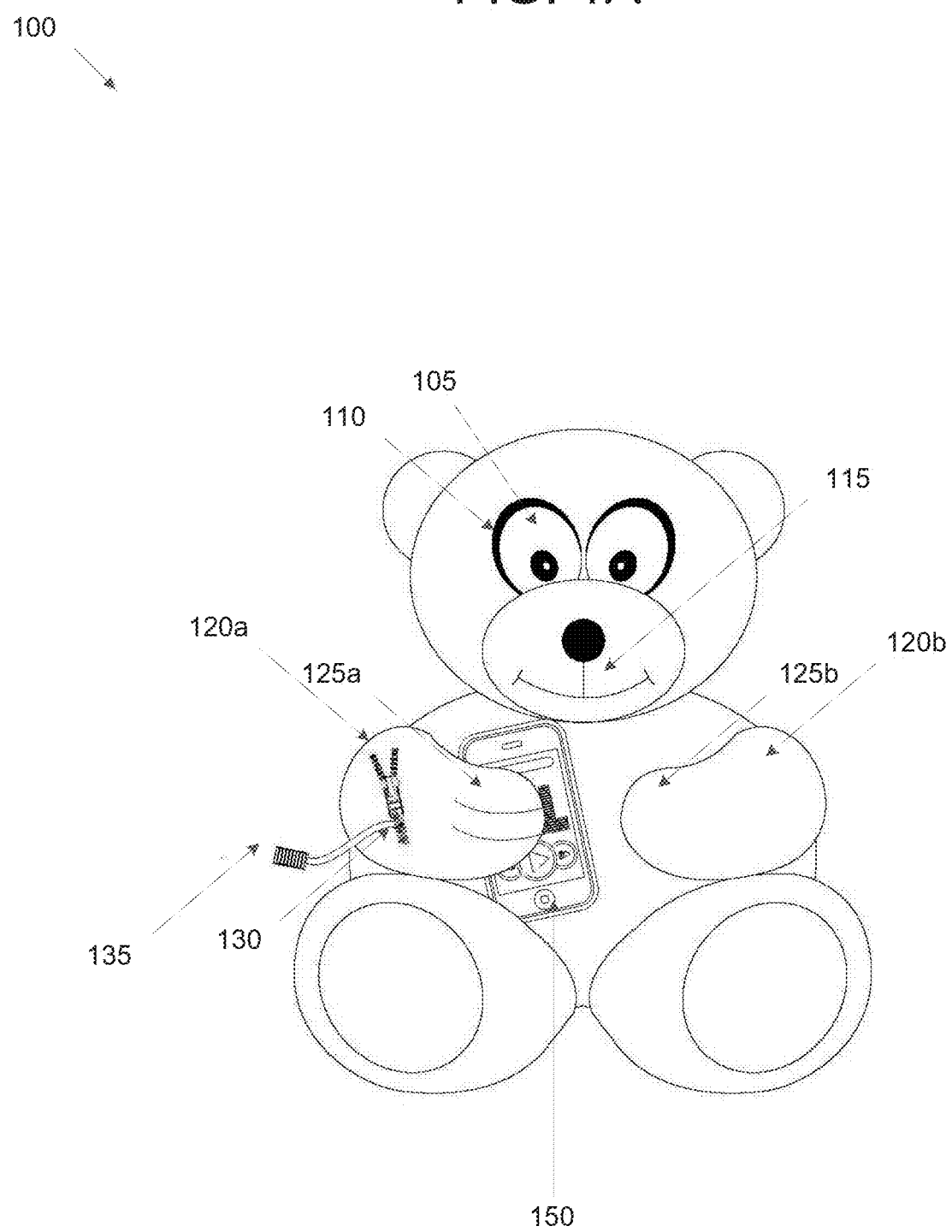
FIGS. 1A through 1D illustrate different front views of an apparatus, according to an embodiment of the present invention.

One or more embodiments may pertain to a toy character (hereinafter "apparatus") that a child can associate with. For example, the apparatus may include a motor configured to cause eyelids of the apparatus to close or, in some cases, open and close. A timer may also be included, such that the motor and/or audio may be operated for a predefined time period. During this time period, the apparatus may read a story, for example, while the child is lying in bed.

FIGS. 1A through 1D illustrate different front views of an apparatus 100, according to an embodiment of the present invention. Apparatus 100 may include a set of eyes 105 including eye lids 110. In one embodiment, eye lids 110 may close, or open and close, while reading the story to the child over a predefined time period. As will be discussed in detail below, the time period may be configurable by a user (e.g., a parent) of apparatus 100.

In this embodiment, apparatus 100 may also include a mouth 115 from which audio may be emitted. It should be appreciated that the audio may be emitted from any location of the apparatus in some embodiments. Depending on the configuration of apparatus 100, mouth 115 may open and close while the audio is outputted. As the audio is being outputted from month 115, the volume of the audio may decrease simultaneously with the closing of eyelids 110 over the predefined period of time.

Figure 1B:
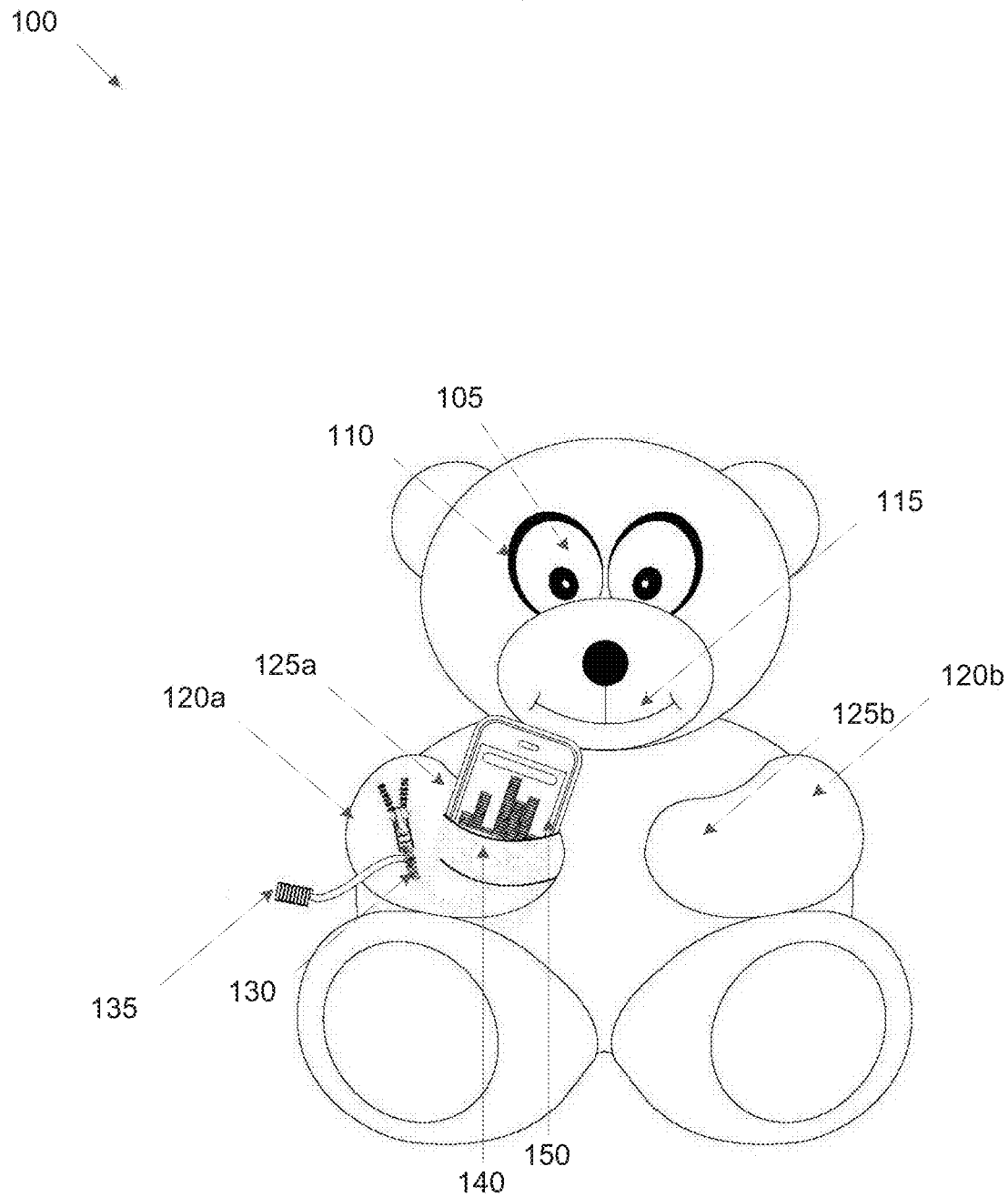
Figure 1C:
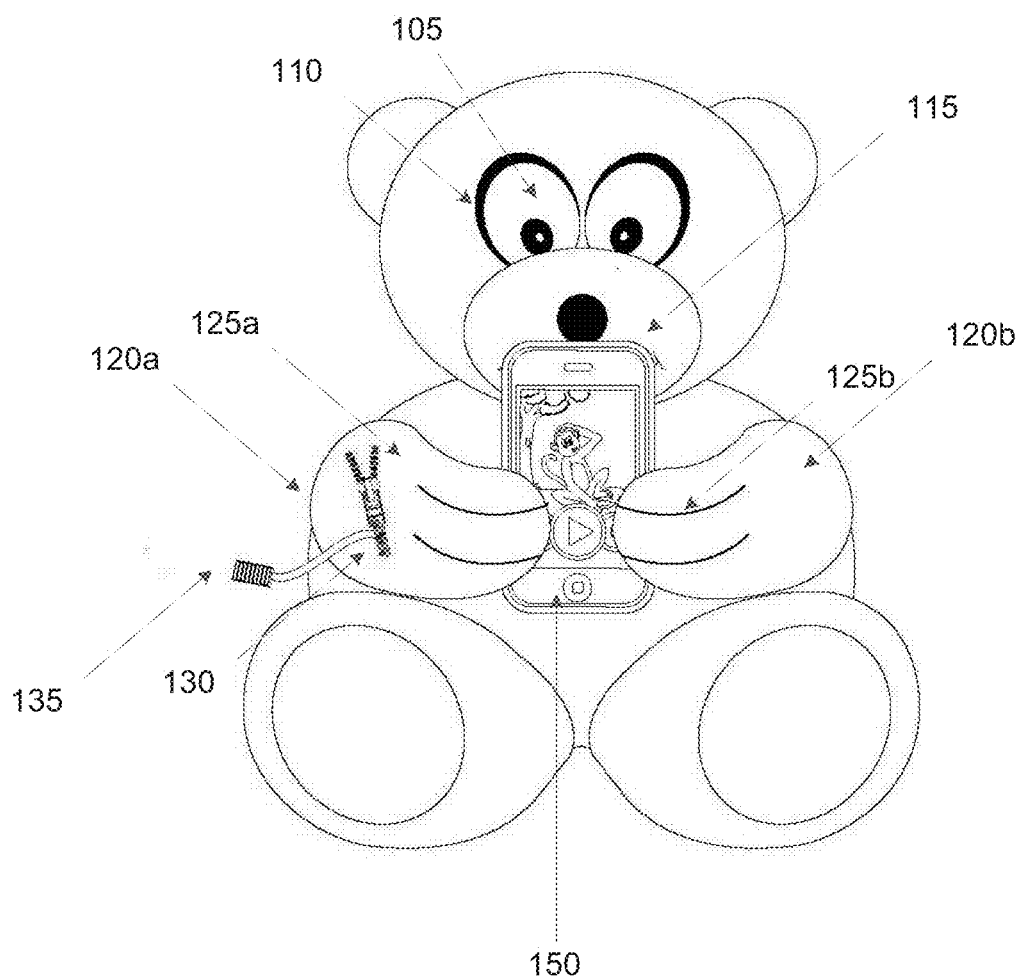
Figure 1D:
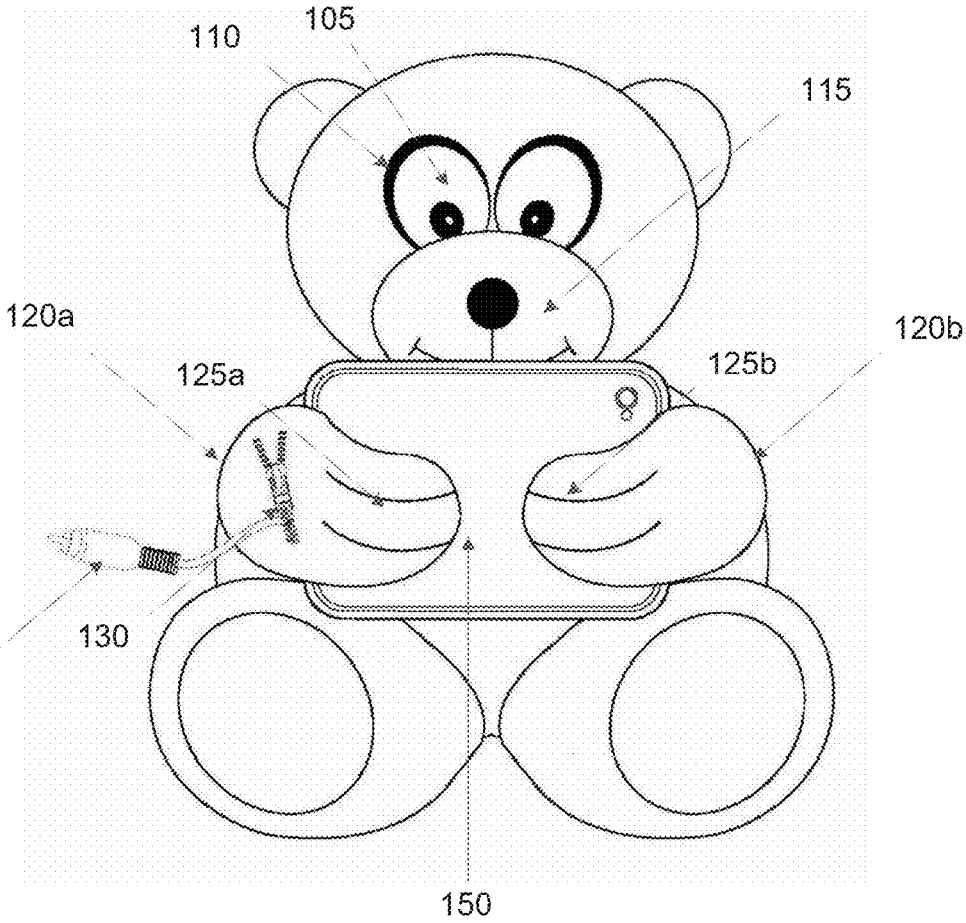

Apparatus 100 may further include arms 120a, 120b having hands 125a, 125b. In certain embodiments, arms 120a, 120b and hands 125a, 125b may move in different and/or unique directions to provide the illusion of an animated appearance by apparatus 100. Hands 125a, 125b may hold a portable device 150, such as a mobile phone or a tablet, providing the effect to the child that apparatus 100 is reading a story on portable device 100. As illustrated in FIG. 1B, apparatus 100 may include a device holder 140 to hold portable device 150.

In another embodiment, apparatus 100 may hold portable device 150 with both hands 125a, 125b. See, for example, FIGS. 1C and 1D. This may be achieved by including slots (not shown) on the inner side of hands 125a, 125b to allow hands 125a, 125b to hold portable device 150. The slots may include a docking mechanism to allow portable device 150 to connect with apparatus 100. Such embodiments may provide the child with the illusion that apparatus 100 is holding portable device 150 and reading the story with the child. It should be appreciated that in some embodiments, the child may watch cartoons, music videos, etc., while apparatus 100 is holding portable device 150. See, for example, FIG. 1C.

As shown in FIGS. 1A through 1D, media cable 135 may be placed within a pocket of apparatus 100, and may be accessed via front zipper 130. In this embodiment, media cable 135 may be a RCA cable, a High Definition Multi-Media Interface (HDMI) cable, a Universal Serial Bus (USB) cable, etc., and may connect portable device 150 with the media device (e.g., media player/recorder 315 of FIG. 3) situated within apparatus 100. In this embodiment, media input/output cable 135 may connect to portable device 150 in this embodiment. However, in other embodiments, input/output cable 135 may connect to a radio, a cassette player, a CD player, a DVD player, or any media device as would be readily appreciated by a person of ordinary skill in the art.

In one example, by connecting media input/output cable 135 to portable device 150, the media player/recorder is configured to cause a speaker (not shown) to play audio from a portable device or, in some embodiments, the media player/recorder may record the audio from portable device 150. In another example, a parent may read a story and record the story in a storage unit (not shown) of the media player/recorder to allow the child to listen to the story at a later time. For example, media input/output cable 135 may connect with a microphone to enable the media player/recorder to record and store the parent's voice while he or she is reading the story. This may provide additional comfort to the child, because the child will be listening to his or her parent's voice as apparatus 100 is reading the story.

Figure 2A:
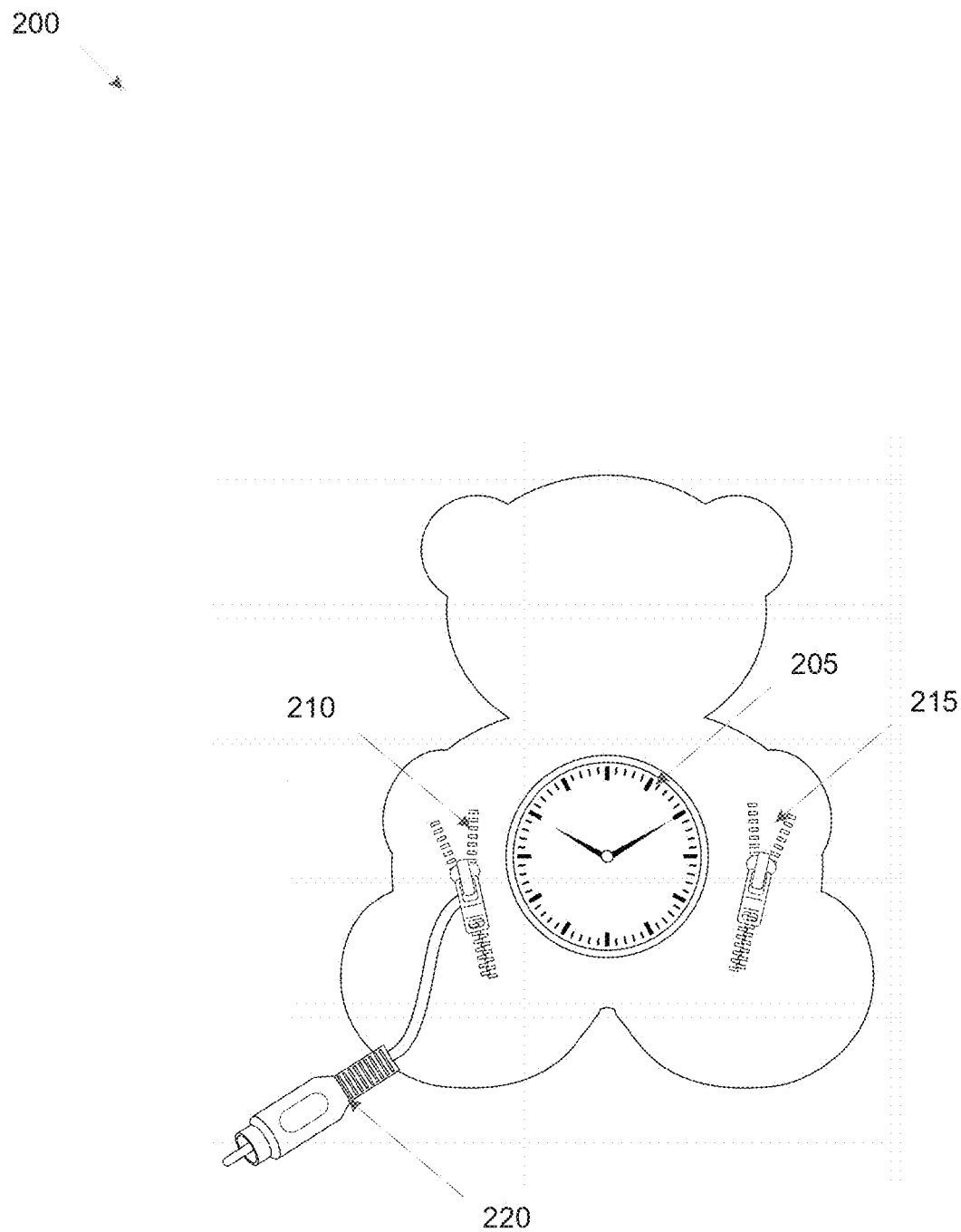
FIGS. 2A and 2B illustrate different rear views of the apparatus, according to an embodiment of the present invention.
Figure 2B:
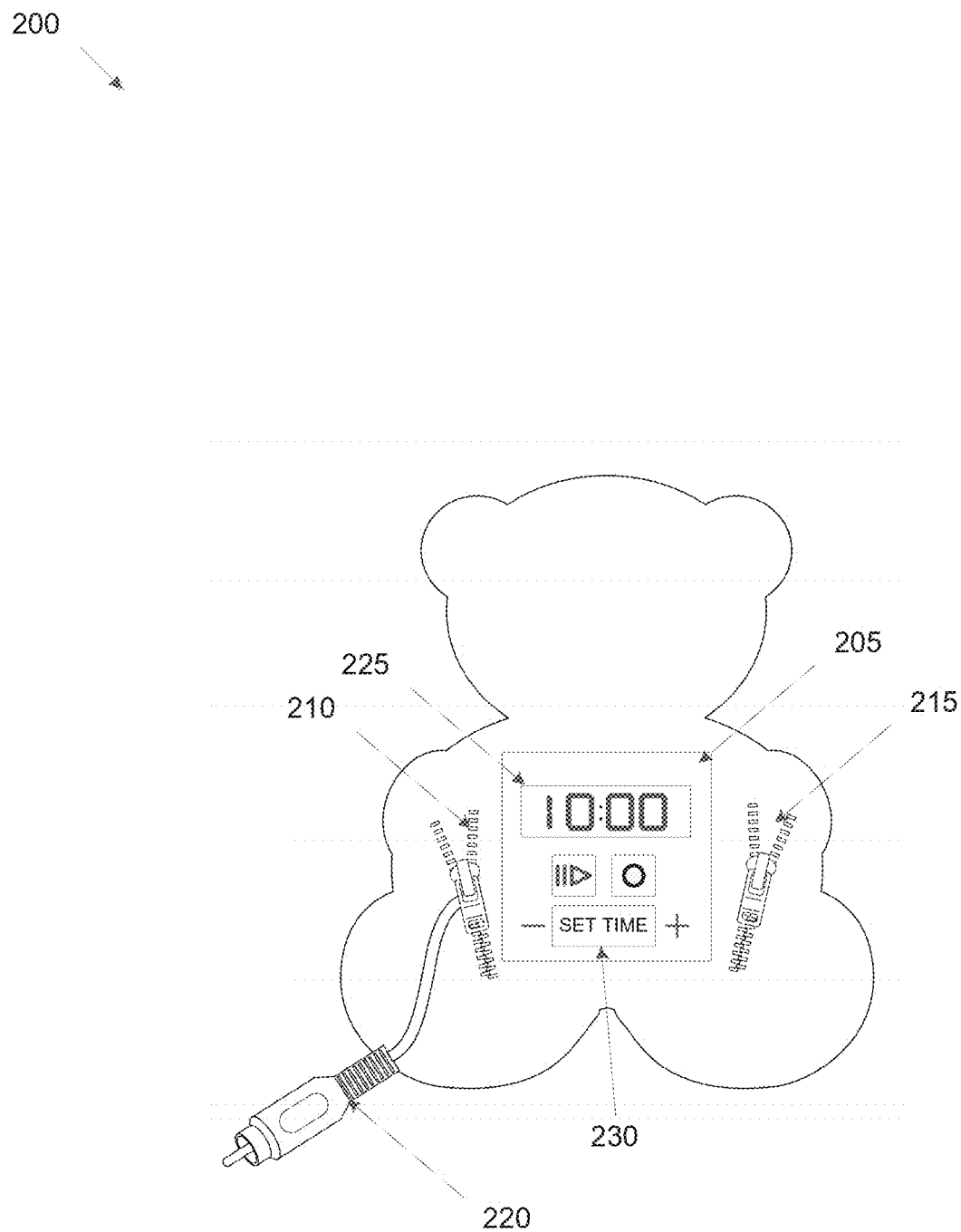

FIGS. 2A and 2B are rear views of apparatus 200, according to an embodiment of the present invention. In this embodiment, apparatus 200 may include a patch (not shown) configured to hide a timer 205. Timer 205 may be a manual timer (see FIG. 2A) or a digital timer (see FIG. 2B) that may be set by the user. The digital timer may include a display unit 225 and buttons 230 to enable the user to play/pause audio, record audio, or set the digital timer using buttons such as plus + or minus –.

Based on the time set by the user, when the user presses the play button, apparatus 200 may play the audio of (i.e., read) the story from either the media player/recorder or the portable device for the predefined period of time. For example, if the user set the time to 10 minutes on timer 205, apparatus 200 may play the audio (i.e., read the story) for 10 minutes. During this time, the eyelids of the apparatus (see FIGS. 1A through 1D) may slowly close and, simultaneously, the volume of the audio may also be reduced. This will assist the child to fall asleep without the parent reading the story to his or her child.

It should be noted that by allowing a parent to set a predefined period of time that a story is played by apparatus 200, the parent may adjust the predefined period of time according to the child. For example, if it takes 20 minutes for the child to fall asleep, the parent may set the time on timer 205 for 20 minutes. As each day passes by and the child falls asleep more quickly, the parent may reduce the predefined period of time on timer 205. For example, during the first week, if it took 20 minutes for the child to fall asleep, and then the next week it took 15 minutes for the child to fall asleep, the parent may choose to reduce the predefined period of time on timer 205, such that apparatus 200 may provide the illusion of falling asleep more quickly as each week passes by. Stated differently, timer 205 allows the parent to set any time based on his or her child's needs.

Apparatus 200 may also include a first zipper 210 and a second zipper 215. First zipper 210, when zipped up, is configured to hide media cable 220 within a pocket of apparatus 200. Media cable 220 is configured to connect a portable device to apparatus 200. In this embodiment, media cable 220 may be a RCA cable, a HDMI cable, a USB cable, etc., and may connect the portable device with the media player/recorder within apparatus 200.

When the portable device is connected with apparatus 200, the media player/recorder cause a speaker to play the audio stored in the portable device, or may record the audio from the portable device, allowing the audio to be stored in a storage unit of the media player/recorder. Second zipper 215, when zipped up, is configured to hide the media player/recorder and the power supply within another pocket of apparatus 200. This may allow the user, amongst other things, to replace or recharge the power supply or increase the storage capacity in the media player/recorder.

Figure 3:
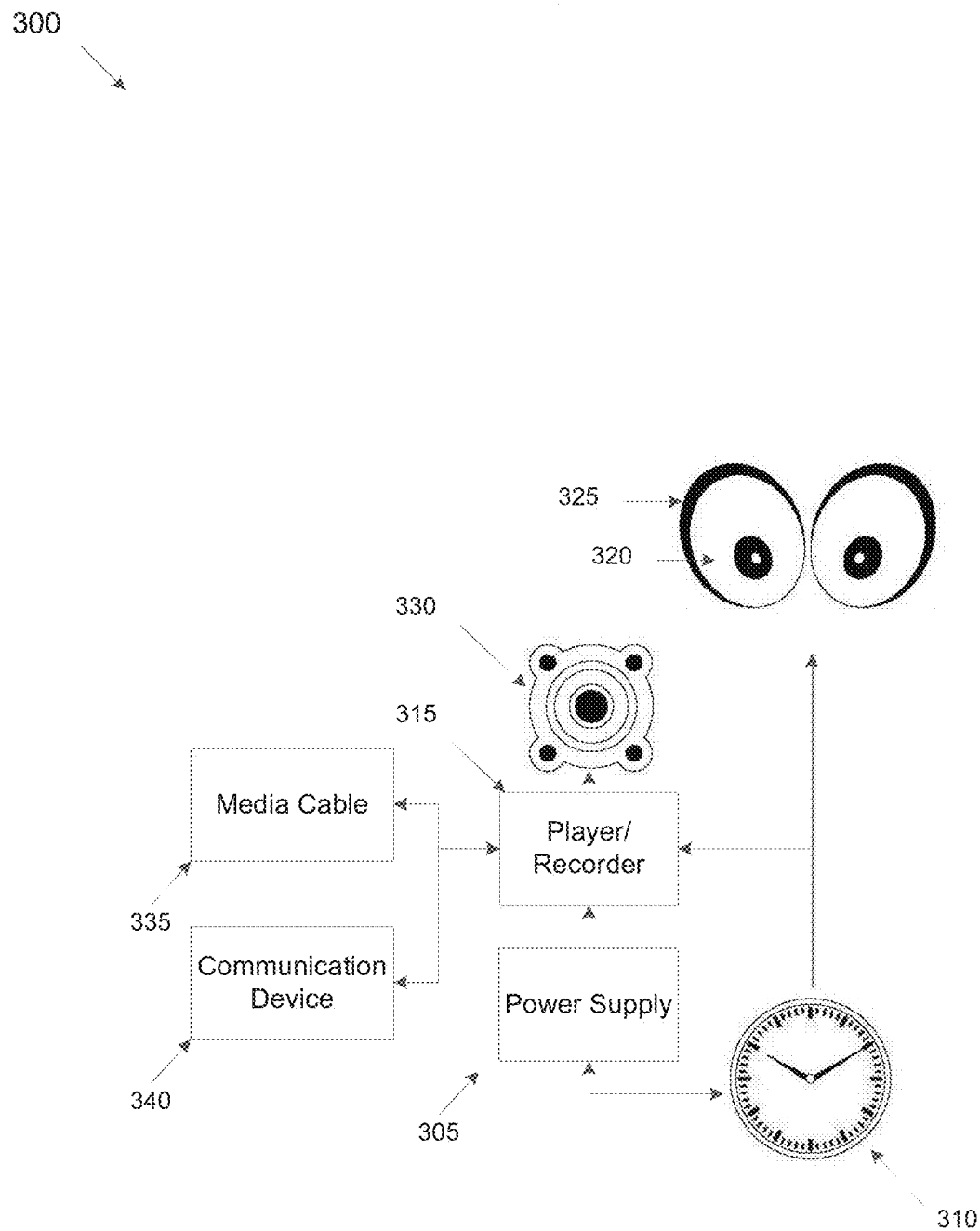
FIG. 3 is a block diagram illustrating a circuit block of the apparatus, according to an embodiment of the present invention.

FIG. 3 is a block diagram 300 illustrating a circuit block of the apparatus, according to an embodiment of the present invention. The circuit block may include a power supply 305 connected to, and configured to provide power to, a timer 310 and a media player/recorder 315. Timer 310 is connected to media player/recorder 315 and eyelids 325. Eyelids 325 are associated with eyes 320. This allows timer 310 to control the level of volume outputted from media player/recorder 315 as well as control the closing of the eyelids of the apparatus. In certain embodiments, timer 310 may reduce the speed at which eyelids 325 open and close. Because there is a two-way connection between timer 310 and power supply 305, when the predefined time period is completed (e.g., at 00:00), power supply 305 may be configured to shut down.

In this embodiment, media player/recorder 315 is configured to control the level of volume (e.g., audio volume) outputted from speaker 330. For example, based on the predefined period of time set in timer 310, media player/recorder 315 is configured to reduce the level of volume outputted from speaker 330.

As discussed above, media player/recorder 315 may include a storage unit (not shown) configured to store media, e.g., audio, video, or both. For example, the storage unit may allow the user to record audio or video to the storage unit of media player/recorder 315 when a portable device is connected to media player/recorder 315 via media cable 335. In another embodiment, when the portable device is connected to media player/recorder 315 via media cable 335, media player/recorder 315 is configured to extract the audio stored in the portable device and output the audio from speaker 330.

In some embodiments, the portable device may connect to apparatus via communication device 340. Communication device 340 may be a Bluetooth® device, a wireless network device, or any wireless communication device configured to wirelessly connect the portable device with the apparatus, as well as control the apparatus. For example, communication device 340 may be configured to wirelessly record audio from the portable device onto the storage unit of media player/recorder 315 and/or wirelessly control functional operations of the apparatus. Functional operations, in this embodiment, may include movement of eye lids 325, movement of arms, volume level of the apparatus, etc.

In certain embodiments, media player/recorder 315 may receive at least one instruction from an external device via media cable 335 or communication device 340. The at least one instruction may instruct the media player/recorder 315 to store audio from the portable device (e.g., external device), play audio for a predefined period of time, or both. The at least one instruction may also cause the motor shown in FIG. 4 to move any part of the apparatus, e.g., move the set of eye lids, move a first arm and a second arm, move a first leg and a second leg, or any part that would be readily appreciated by a person of ordinary skill in the art.

Figure 4:
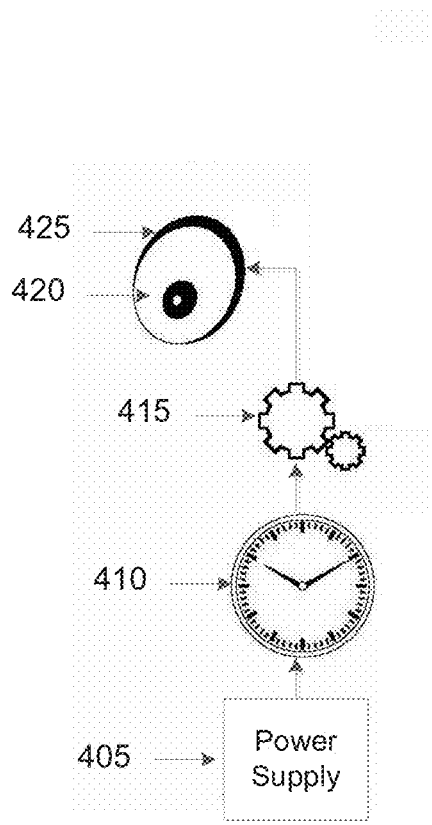
FIG. 4 is a diagram illustrating a motor system in the apparatus, according to an embodiment of the present invention.

FIG. 4 is a block diagram 400 illustrating a motor system of the apparatus, according to an embodiment of the present invention. The motor system provided herein may be configured to move eyelids 425 in an up and down manner, or otherwise open or close eyelids 425 in any suitable direction based on the configuration of the apparatus, such that eyelids 425 may appear to open and close as audio is being outputted from the apparatus.

In this embodiment, power supply 405 may provide power to timer 410 and, either directly or indirectly, to motor 415. During operation of the apparatus, as the predefined period of time elapses on timer 410, motor 415 may slowly begin to move eyelids 425 from an open state to a closed state. Stated differently, motor 415 may act to close eyelids 425 from an open state to a closed state.

In another embodiment, motor 415 may slowly move eyelids 425 up and down over the predefined period of time such that it appears that eyelids 425 are closing and opening. Once the predefined period of time has expired on timer 410, motor 415 may move eyelids 425 from an opened state to a closed state to provide the effect that the apparatus is in a sleep state.

Figure 5:
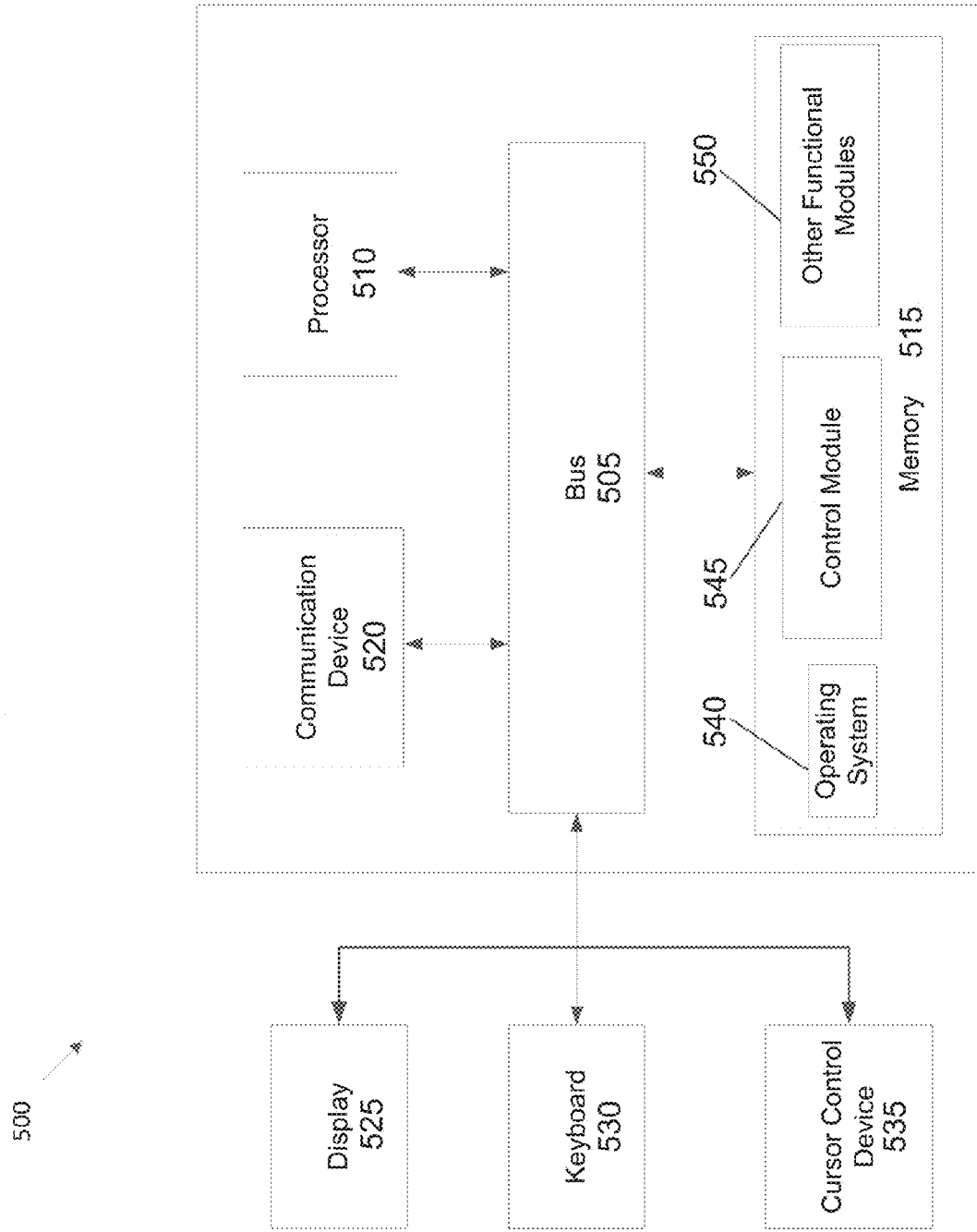
FIG. 5 is a block diagram illustrating a computing system of a portable device, according to an embodiment of the present invention.

FIG. 5 is a block diagram 500 illustrating a computing device, according to an embodiment of the present invention. The computing device may be a portable device, such as a mobile device or tablet, or any other device that would be appreciated by a person of ordinary skill in the art.

Computing device 500 includes a bus 505 or other communication mechanism for communicating information, and a processor 510 coupled to bus 505 for processing information. Processor 510 may be any type of general or specific purpose processor, including a central processing unit (CPU) or application specific integrated circuit (ASIC). Computing device 500 further includes a memory 515 for storing information and instructions to be executed by processor 510. Memory 515 can be comprised of any combination of random access memory (RAM), read only memory (ROM), flash memory, cache, static storage such as a magnetic or optical disk, or any other types of non-transitory computer-readable media or combinations thereof. Additionally, computing device 500 includes a communication device 520, such as a wireless network interface card, USB device, Bluetooth®, or any media communication unit, to provide access to a network or wirelessly connect with the apparatus, such as that illustrated in FIGS. 1A through 1D. Computing device 500 may also include a port. The port may allow a media cable shown in FIG. 1A, for example, to connect computing device 500 with apparatus 100 of FIG. 1A.

Non-transitory computer-readable media may be any available media that can be accessed by processor 510 and may include both volatile and non-volatile media, removable and non-removable media, and communication media. Communication media may include computer-readable instructions, data structures, program modules or other data in a modulated data signal such as a carrier wave or other transport mechanism and includes any information delivery media.

Processor 510 is further coupled via bus 505 to a display 525, such as a Liquid Crystal Display (LCD), for displaying information to a user. A keyboard 530 and a cursor control device 535 may be coupled to bus 505 to enable a user to interface with computing device 500.

In one embodiment, memory 515 stores software modules that provide functionality when executed by processor 510. The modules include an operating system 540 for computing device 500. The modules further include a control module 545 that is configured to control an apparatus, as shown in FIGS. 1A through 1D, for example.

Control module 545 may allow a user to set a timer on the apparatus for any length of time, as well as set a schedule of operation for the apparatus. For example, if a parent wants the apparatus to operate for 20 minutes during the first week, 15 minutes the third week, and 10 minutes the fourth week, control module 545 may enable the user to configure the apparatus to operate for a predefined period of time by setting a schedule of operation. Control module 545 may also enable the user to activate and deactivate the apparatus, as well as enable the user to record or store audio or video that can be played from computing device 500.

Control module 545 may also allow the user of computing device 500 to control movement of the apparatus shown in FIGS. 1A-1D, for example. For instance, control module 545 may remotely activate and deactivate the apparatus, control movement of the arms and legs of the apparatus, control the state of the eye lids (e.g., close state and open state), control opening and closing of the eye lids, etc. In certain embodiments, control module 545 may control laughter from the apparatus. For example, if the user desires to have the apparatus provide a tickling sound effect, the user may utilize control module 545 to achieve this result.

Computing device 500 may include one or more additional functional modules 550 that include additional functionality. For example, functional modules 550 may include separate modules, such as an audio module to control the volume of the apparatus. Functional modules 550 may also include a voice module to control to the type of voice (e.g., male voice or female voice) outputted from the apparatus.

One skilled in the art will appreciate that a "system" could be embodied as a personal computer, a server, a console, PDA, a mobile phone, a tablet computing device, or any other suitable computing device, or combination of devices. Presenting the above-described functions as being performed by a "system" is not intended to limit the scope of the present invention in any way, but is intended to provide one example of many embodiments of the present invention. Indeed, methods, systems and apparatuses disclosed herein may be implemented in localized and distributed forms consistent with computing technology, including cloud computing systems.

It should be noted that some of the system features described in this specification have been presented as modules, in order to more particularly emphasize their implementation independence. For example, a module may be implemented as a hardware circuit comprising custom very large scale integration (VLSI) circuits or gate arrays, off-the-shelf semiconductors such as logic chips, transistors, or other discrete components. A module may also be implemented in programmable hardware devices such as field programmable gate arrays, programmable array logic, programmable logic devices, graphics processing units, or the like.

A module may also be at least partially implemented in software for execution by various types of processors. An identified unit of executable code may, for instance, comprise one or more physical or logical blocks of computer instructions that may, for instance, be organized as an object, procedure, or function. Nevertheless, the executables of an identified module need not be physically located together, but may comprise disparate instructions stored in different locations which, when joined logically together, comprise the module and achieve the stated purpose for the module. Further, modules may be stored on a computer-readable medium, which may be, for instance, a hard disk drive, flash device, random access memory (RAM), tape, or any other such medium used to store data.

Indeed, a module of executable code could be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network.

One or more embodiments of the present invention pertain to an apparatus that includes a set of eyes and eyelids. The apparatus also includes a media input/output unit configured to output audio from the apparatus or a portable device. The eyelids are configured to close while the audio is outputted from the media input/output unit. This provides the illusion to the child that the apparatus is falling asleep while the apparatus is reading the story to the child. This may cause the child to fall asleep without the parent's assistance.

It will be readily understood that the components of the invention, as generally described and illustrated in the figures herein, may be arranged and designed in a wide variety of different configurations. Thus, the detailed description of the embodiments is not intended to limit the scope of the invention as claimed, but is merely representative of selected embodiments of the invention.

The features, structures, or characteristics of the invention described throughout this specification may be combined in any suitable manner in one or more embodiments. For example, the usage of "certain embodiments," "some embodiments," or other similar language, throughout this specification refers to the fact that a particular feature, structure, or characteristic described in connection with an embodiment may be included in at least one embodiment of the invention. Thus, appearances of the phrases "in certain embodiments," "in some embodiments," "in other embodiments," or other similar language, throughout this specification do not necessarily all refer to the same embodiment or group of embodiments, and the described features, structures, or characteristics may be combined in any suitable manner in one or more embodiments.

One having ordinary skill in the art will readily understand that the invention as discussed above may be practiced with steps in a different order, and/or with hardware elements in configurations that are different than those which are disclosed. Therefore, although the invention has been described based upon these preferred embodiments, it would be apparent to those of skill in the art that certain modifications, variations, and alternative constructions would be apparent, while remaining within the spirit and scope of the invention. In order to determine the metes and bounds of the invention, therefore, reference should be made to the appended claims.

The invention claimed is:

1. An apparatus, comprising:
a set of eyes and a set of eyelids connected to a motor, the motor configured to move the set of eyelids;
a media player/recorder configured to play audio via a speaker for a predefined period of time; and
a timer connected to the motor and the media player/recorder, and configured to control operation of the motor and the audio for the predefined period of time, the audio comprising a children storybook, a song, or both, wherein
during operation of the motor and the audio, the timer is configured to cause the motor to move the set of eyelids in one direction, gradually transitioning the set of eyelids from an open state to a closed state over the predefined period of time while playing the audio,
the predefined period of time is a length of the audio,
the timer comprises a first button to increase, and a second button to decrease, the predefined period of time,
the increase of the predefined period of time increases a playtime for the audio and a time period for transitioning the set of eyelids from the open state to the closed state, and
the decrease of the predefined period of time decreases the playtime for the audio and the time period for transitioning the set of eyelids from the open state to the closed state.

2. The apparatus of claim 1, wherein the timer is further configured to control operation of the media player/recorder to reduce a volume of the audio over the predefined period of time.

3. The apparatus of claim 2, wherein the media player/recorder is further configured to play the audio via the speaker when an external device is connected to the apparatus.

4. The apparatus of claim 2, wherein the media player/recorder comprises a storage device to record and store the audio from an external device.

5. The apparatus of claim 1, further comprising:
a device holder configured to hold a portable device, wherein
the device holder comprises a pouch located on an arm of the apparatus, or a pair of slots on two arms of the apparatus, to hold the portable device.

6. The apparatus of claim 1, further comprising:
a cable configured to connect a portable device with the apparatus.

7. An apparatus, further comprising:
a set of eyes and a set of eyelids connected to a motor, the motor configured to move the set of eyelids;
a media player/recorder configured to output audio via a speaker for a predefined period of time; and
a timer connected to the motor and the media player/recorder, and configured to provide timing information to the media player/recorder and control operation of the motor to move the set of eyelids in one direction, gradually transitioning the set of eyelids from an open state to a closed state over the predefined period of time while outputting the audio, the audio comprising a children story book, song, or both, wherein
the timer is further configured to cause the media player/recorder to decrease volume of the audio, and simultaneously transition the set of eyelids from the open state to the closed state, via the motor, over the predefined period of time,
the predefined period of time is a length of the audio, and
the timer comprises a first button to increase, and a second button to decrease, the predefined period of time,
the increase of the predefined period of time increases a playtime for the audio and a time period for transitioning the set of eyelids from the open state to the closed state, and
the decrease of the predefined period of time decreases the playtime for the audio and the time period for transitioning the set of eyelids from the open state to the closed state.

8. The apparatus of claim 7, wherein the media player/recorder is further configured to output the audio for the predefined period of time when an external device is connected to the apparatus.

9. The apparatus of claim 7, wherein the media player/recorder comprises a storage device configured to record the audio from an external device.

10. The apparatus of claim 9, wherein the media player/recorder is further configured to output the recorded audio for the predefined period of time.

11. The apparatus of claim 7, further comprising:
a first arm and a second arm, wherein at least one of the first arm and the second arm are configured to hold an external device.

12. The apparatus of claim 11, wherein the first arm, the second arm, or both, comprise a holder configured to hold the external device.

13. The apparatus of claim 7, further comprising:
a communication device configured to connect an external device with the media player/recorder of the apparatus, the speaker of the apparatus, or both.

14. The apparatus of claim 7, wherein the media player/recorder is configured to receive at least one instruction from an external device via a media cable or a communication device.

15. The apparatus of claim 14, wherein the at least one instruction is configured to instruct the media player/recorder to store audio from the external device, play audio for the predefined period of time, or both.

16. The apparatus of claim 14, wherein the at least one instruction is further configured to cause the motor to move any part of the apparatus.

* * * * *